(12) United States Patent
MacDonald

(10) Patent No.: US 8,121,705 B2
(45) Date of Patent: Feb. 21, 2012

(54) MRI-SAFE DEFIBRILLATOR ELECTRODES

(75) Inventor: Stuart G. MacDonald, Pultneyville, NY (US)

(73) Assignee: Medtronic, Inc., Minneapolis, MN (US)

( * ) Notice: Subject to any disclaimer, the term of this patent is extended or adjusted under 35 U.S.C. 154(b) by 537 days.

(21) Appl. No.: 12/147,237

(22) Filed: Jun. 26, 2008

(65) Prior Publication Data

US 2009/0005825 A1   Jan. 1, 2009

Related U.S. Application Data

(60) Provisional application No. 60/946,411, filed on Jun. 27, 2007.

(51) Int. Cl.
*A61N 1/05* (2006.01)
(52) U.S. Cl. .................. 607/115; 607/119
(58) Field of Classification Search .............. 607/2, 4, 607/5, 115, 116, 119
See application file for complete search history.

(56) References Cited

U.S. PATENT DOCUMENTS

| | | | |
|---|---|---|---|
| 4,641,656 A * | 2/1987 | Smits | 607/5 |
| 4,738,734 A | 4/1988 | Ziemek | |
| 4,841,259 A | 6/1989 | Mayer | |
| 4,926,862 A | 5/1990 | Miyajima et al. | |
| 5,317,665 A | 5/1994 | Herrebrugh | |
| 5,433,732 A | 7/1995 | Hirschberg et al. | |
| 5,490,035 A | 2/1996 | Yen et al. | |
| 5,496,359 A | 3/1996 | Davidson | |
| 5,917,157 A | 6/1999 | Remsburg | |
| 6,184,324 B1 | 2/2001 | Benz et al. | |
| 6,187,028 B1 | 2/2001 | Munshi | |
| 6,426,861 B1 | 7/2002 | Munshi | |
| 6,451,947 B1 | 9/2002 | Benz et al. | |
| 6,514,276 B2 | 2/2003 | Munshi | |
| 6,795,730 B2 | 9/2004 | Connelly et al. | |
| 6,875,180 B2 | 4/2005 | Weiner et al. | |
| 7,801,625 B2 * | 9/2010 | MacDonald | 607/119 |
| 2001/0011183 A1 | 8/2001 | Munshi | |
| 2002/0082673 A1 | 6/2002 | Benz et al. | |
| 2003/0120197 A1 | 6/2003 | Kaneko et al. | |
| 2003/0176893 A1 | 9/2003 | Munshi | |
| 2003/0204217 A1 | 10/2003 | Greatbatch | |
| 2004/0199069 A1 | 10/2004 | Connelly et al. | |

(Continued)

FOREIGN PATENT DOCUMENTS

WO       03/061755 A    7/2003

OTHER PUBLICATIONS

International Search Report for corresponding International Patent Application No. PCT/US2008/068514, mailed Oct. 13, 2008.

*Primary Examiner* — Brian T Gedeon
(74) *Attorney, Agent, or Firm* — Stephen W. Bauer; Michael J. Ostrom

(57) ABSTRACT

The present invention reduces patient risks associated with RF-induced thermogenic tissue damage and with pulsed gradient-field-induced arrhythmias by using a defibrillator lead having a self-healing dielectric material that prevents induced voltages from MRI equipment from damaging an ICD or causing unintended defibrillation shocks to a patient. Another aspect of the present invention utilizes a sliding contact arrangement to prevent induced voltages from MRI equipment from being electrically coupled to an ICD thereby reducing patient risks associated with RF-induced thermogenic tissue damage and with pulsed gradient-field-induced arrhythmias.

14 Claims, 2 Drawing Sheets

U.S. PATENT DOCUMENTS

| | | |
|---|---|---|
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0283167 A1 | 12/2005 | Gray |
| 2006/0271138 A1* | 11/2006 | MacDonald .................. 607/119 |

* cited by examiner

MRI-SAFE DEFIBRILLATOR ELECTRODES

CROSS-REFERENCE TO RELATED APPLICATION

This application claims the benefit of U.S. Provisional Application No. 60/946,411 filed Jun. 27, 2007.

FIELD OF THE PRESENT INVENTION

The present invention is directed to a defibrillator electrode. More particularly, the present invention is directed to a defibrillator electrode that can be used in a magnetic resonance imaging environment.

BACKGROUND OF THE PRESENT INVENTION

Various approaches have been taken to reduce or eliminate the risks associated with patients having implanted medical devices who need magnetic resonance imaging (MRI) examinations.

However, the specific characteristics and requirements of defibrillator systems create unique challenges. Unlike pacemaker, drug pump, and neurostimulation devices, implantable cardioverter defibrillators (ICDs) not only sense and pace the heart in a manner similar to a pacemaker, but also may release electrical energy in pulses of up to 40 Joules and at an excess of 800 volts and 10 amps if ventricular fibrillation (VF) or other anomalous conditions are sensed.

While this may occur very rarely, prior art solutions to thermogenic tissue risks associated with the radio frequency (RF) fields used in magnetic resonance imaging in some cases utilize small electrical components that can be damaged in the presence of electrical potentials and currents of this magnitude. Specifically, the miniature inductive, capacitive, and semiconductor components that may be packaged in the electrode assembly of a pacemaker lead are typically rated for potential and current levels far below those used in defibrillation.

Thus, it is desirable to provide a defibrillation electrode that enables highly reliable operations over the life of the ICD implant in a patient, but such that when the patient is placed in the bore of a magnetic resonance imaging system, all sources of RF-induced energy and gradient-field-induced energy that could harm the patient are totally isolated electrically, thus providing complete safety for the patient.

SUMMARY OF THE PRESENT INVENTION

One aspect of the present invention utilizes a self-healing dielectric material that prevents induced voltages from MRI equipment from damaging an ICD or causing unintended defibrillation shocks to a patient thereby reducing patient risks associated with RF-induced thermogenic tissue damage and with pulsed gradient-field-induced arrhythmias.

Another aspect of the present invention utilizes a sliding contact arrangement to prevent induced voltages from MRI equipment from being electrically coupled to an ICD thereby reducing patient risks associated with RF-induced thermogenic tissue damage and with pulsed gradient-field-induced arrhythmias.

DETAILED DESCRIPTION OF THE PREFERRED EMBODIMENTS

Figure 1:
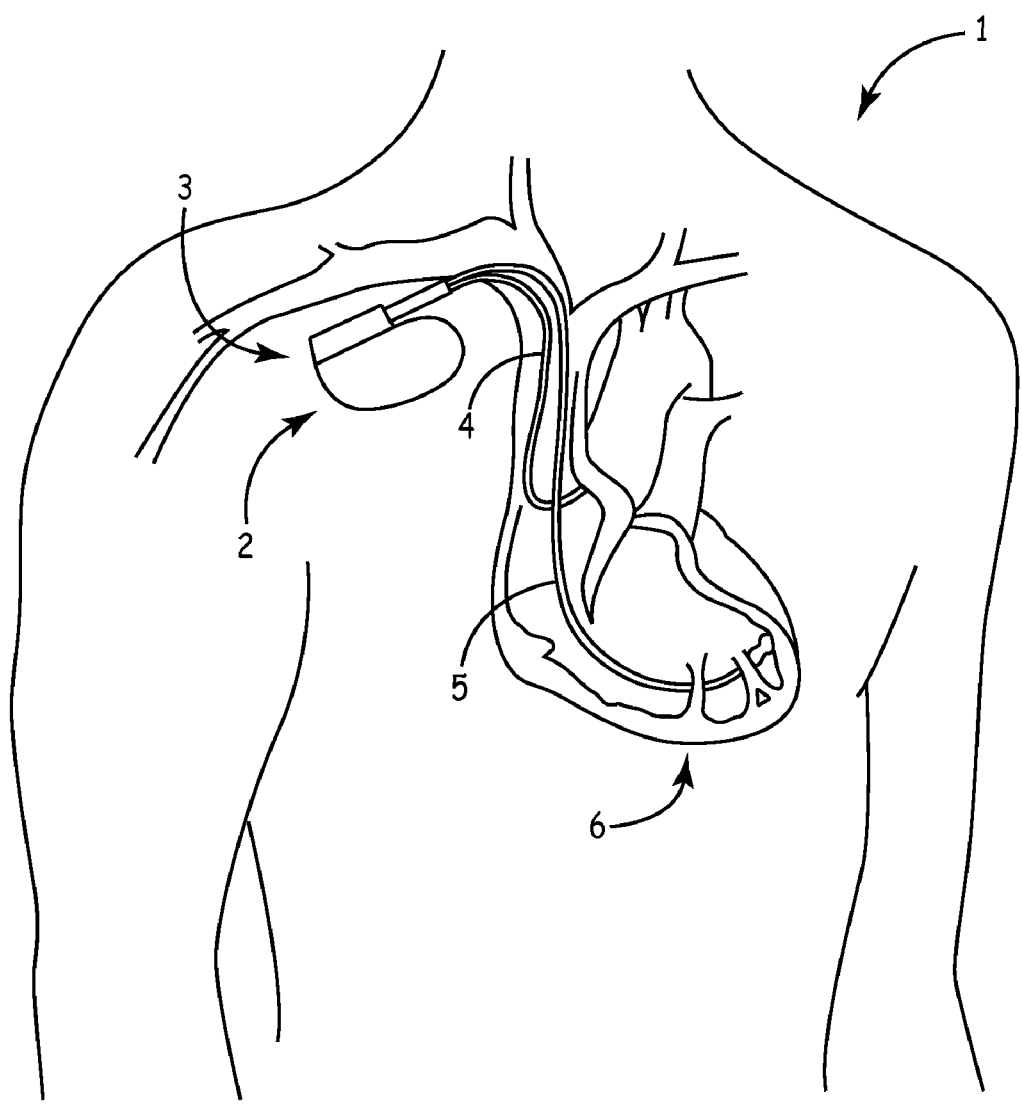
FIG. 1 illustrates a patient having an implantable cardioverter defibrillator utilizing a defibrillator lead in accordance with the present invention.

FIG. 1 illustrates a patient 1 having a cardioverter defibrillator 2 implanted in the right shoulder area 3. A lead 4 is shown extending into the right atria of the patients heart 6, while another lead 5 is shown extending into the right ventricle of the heart 6. The ventricular lead 5 comprises a pacing/defibrillation lead capable of pacing the heart 6 in the event an intrinsic heart beat is not detected. The lead 5 can also deliver a defibrillation pulse (shock) to the patient in the event that the defibrillator 2 determines that a life threatening arrhythmia is detected.

Figure 2:
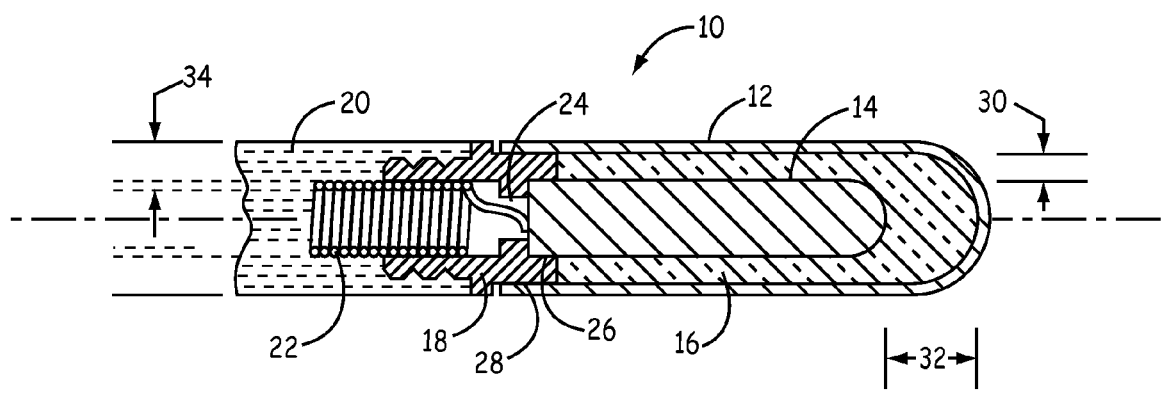
FIG. 2 illustrates a preferred embodiment for the defibrillator lead of FIG. 1.

FIG. 2 shows a preferred embodiment of the tip of the defibrillator lead 15 that uses a self-healing dielectric material, such as disclosed in published US Patent Application, publication number 2006-0271138A1, entitled Electromagnetic Interference Immune Pacing/Defibrillation Lead. Published US Patent Application, publication number 2006-0271138A1, describes various means to employ self-healing dielectric materials in the manufacture of the long conductive structure connecting the implantable cardioverter defibrillator (ICD) 2 to the electrode that rests within the patient's heart. The entire content of published US Patent Application, publication number 2006-0271138A1, is hereby incorporated by reference.

Referring to FIG. 2, electrode assembly 10 has an electrode sheath 12 in contact with cardiac tissue, or in contact with circulating blood in the case of the defibrillation lead in an ICD. Electrode core 14 is centered within electrode sheath 12, the cavity between them being filled with self-healing dielectric material 16 such as described in published US Patent Application, publication number 2006-0271138A1.

As illustrated in FIG. 2, the self-healing dielectric material is located in the electrode assembly itself. By having the self-healing dielectric material located in the electrode assembly, the self-healing dielectric material is not located in the remainder of the lead, thereby simplifying manufacturing and increasing reliability in an implant environment.

Under normal or "standby" conditions, the dielectric material 16, having thickness 30 between the electrode sheath 12 and electrode core 14, resists the flow of electrical current, so unwanted energy associated with RF and gradient field sources is not conducted to the electrode sheath and thus not to the patient's body. Upon application of a potential at a level associated with a defibrillation pulse, the dielectric material 16 breaks down and conducts, permitting delivery of the defibrillation pulse from the ICD to the patient.

The threshold for dielectric breakdown is an inherent feature that depends on the material itself, and the thickness 30; this can be chosen to be far above the levels associated with RF-induced and gradient-field-induced energy, but far below the level employed during defibrillation. Thus, the threshold should be designed to be significantly above 10 volts and significantly below 800 volts. A nominal choice may be made at 100 volts, but may be anywhere between 20 and 600 volts.

Electrode core 14 is held by insulator 18, and is hermetically sealed to it at juncture 26. Filar conductor 22 is also physically captured by insulator 18, providing strain relief and for a reliable solder or weld connection 24 that does not undergo mechanical fatigue from repeated bending. Insulator 18 is also hermetically sealed on its periphery 28 to electrode sheath 12, so that the dielectric material 16 is never exposed to water or ions that would otherwise migrate from blood or body tissues into it and degrade its electrical properties.

The filar lead 22 is encased in jacket material 20, and care is taken to maintain jacket thickness 34 so that the jacket material 20 will not break down and conduct under the high voltage defibrillation pulse.

In order to avoid "corona-like hot spots" that may be the focus of repeated dielectric breakdown, care is taken to design electrode core 14 with a rounded distal end, and to provide adequate axial spacing 32 so that breakdown at the distal end can be avoided and breakdown can rather occur at various locations in the cylindrical volume between the electrode core 14 and the electrode sheath 12.

Various additional features such as the grooves shown on the exterior of insulator 18 to enhance bonding with jacket material 20, and other features relating to the range of defibrillator lead designs currently used to optimize electrophysiological performance (e.g. coil shapes rather than 'bullet' shapes) may be used in concert with the invention described herein.

Figure 3:
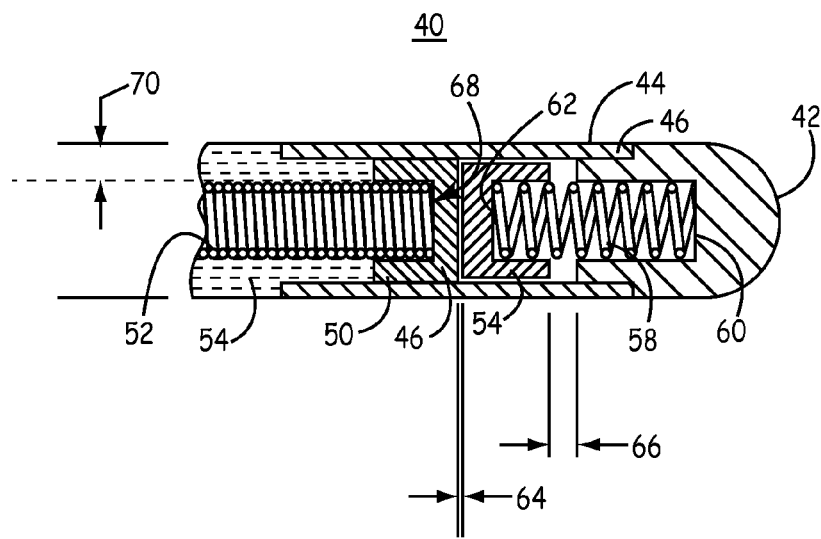
FIG. 3 illustrates another preferred embodiment for the defibrillator lead of FIG. 1.

FIG. 3 illustrates an approach to magnetic resonance imaging safety for an ICD lead that takes advantage of the intense static magnetic field used in magnetic resonance imaging in order to open an otherwise closed contact, and completely isolate the electrode exterior from any RF-induced or gradient-field induced energy during the magnetic resonance imaging examination.

Electrode assembly 40 includes an electrode tip 42 that delivers the defibrillation pulse to the patient when appropriate. It should be noted, as stated above, that various alternative approaches to optimizing electrical contact with the patient's body tissues (e.g. coils vs. 'bullet' shapes) may be readily adapted to the invention disclosed herein.

Electrode tip 42 is connected to insulating sheath 44 by way of a hermetic seal at juncture 46. In like manner, base contact 48 is retained and hermetically sealed to insulating sheath 44 at juncture 50, providing an interior volume that is completely isolated from water or ions in the patient's blood and body tissues. While electrode tip 42 is manufactured from an electrically conductive, hermetically sealable, ferromagnetic, biocompatible material (e.g. cobalt chromium), base contact 48 is manufactured from an electrically conductive, non-magnetic, hermetically sealable, biocompatible material (e.g. titanium or nitinol).

As in the previous design, filar 52 is encased in a jacket 54 having insulating properties and thickness 70 sufficient to withstand the defibrillation pulse without breakdown, and the filar 52 is soldered or welded to base contact 48 at one or more locations 68, thus providing structural support and eliminating fatigue due to repeated bending.

Sliding contact 56 is manufactured from the same or similar electrically conductive, hermetically sealable, ferromagnetic, biocompatible material as is electrode tip 42, and is designed to slide axially within insulating sheath 44 upon application of an axial force. Sliding contact 56 is connected to electrode tip 42 by spring 58. Solder or weld joints at locations 60 and 62 create a path for electrical current flow; spring 58 and solder/weld joints are made from materials and designed to pass pulses of current having magnitudes well beyond those typically used in an ICD (e.g. spring and joints designed with a 3× safety factor over the typical 10 amp pulse will withstand 30 amp pulses).

The spring 58 is designed to provide a modest force, capable of maintain physical contact between base contact 48 and sliding contact 64 under any foreseeable acceleration associated with operation as an implant. Thus, outside of an applied magnetic field, contact gap 64 will essentially be closed, or zero in size. It should be noted that some high-energy switches are "wetted" with metallic liquid mercury, or other contact-enhancing material; a similar approach may be taken with this design but is not required for reliable operation.

When a small magnetic field is applied to the electrode assembly 60, but a field that is less than that found in a magnetic resonance imaging system, a very small attractive force is developed between electrode tip 42 and sliding contact 56 due to the fact that both are ferromagnetic.

Spring 58 is designed to provide sufficient compressive force so that gap 64 is always closed, under both acceleration loads and in the presence of terrestrial magnetic fields that are orders of magnitude smaller than those used in magnetic resonance imaging. The compressive force designed into spring 58, in concert with the materials and masses of tip electrode 42 and sliding contact 56, are chosen so that when the electrode assembly 40 is place within a static magnetic field exceeding 0.05 Tesla, the attractive force created between tip electrode 42 and sliding contact 56 overcomes the compressive force provided by spring 58, resulting in contact gap 64 opening to a spacing equivalent to rest gap 66. As long as the static magnetic field is applied, contact gap 64 will remain open, and the electrode tip 42 will remain electrically isolated from RF-induced and gradient-field-induced sources of energy.

In a first embodiment, rest gap 66 may be designed so that when it is closed by the static magnetic field and contact gap 64 opens, the spacing is sufficient to withstand a 1000 volt applied potential without arcing. In this first embodiment, the ICD will be unable to deliver a defibrillation pulse even if the need is detected; this approach may be appropriate if there is a significant probability that the logic circuits within the ICD pulse generator can be disrupted by the magnetic resonance imaging system and deliver one or more defibrillation pulses that are actually not appropriate, and that the risk to the patient resulting from this is higher than the risk associated with not being defibrillated in the event it is actually needed during the magnetic resonance imaging procedure.

In a second embodiment, rest gap 66 may be designed to have a dimension such that when closed by the magnetic resonance imaging static magnetic field contact gap 64 is opened to a dimension that is large enough so that electrical potentials associated with RF-induced and gradient-field-induced energies will not conduct or arc between sliding contact 56 and base contact 48, but this dimension is small enough that when the electrical potential between sliding contact 56 and base contact 48 is at a level typically used in a defibrillation pulse, and an electrical arc conducts this electrical pulse to the tip electrode 42, permitting defibrillation of the patient's heart. It can be seen that in this second embodiment, the ICD may retain its full functionality while the patient is protected from risks associated with RF-induced thermogenic tissue damage and gradient-field-induced arrhythmia.

In either the first or second embodiments described above, the volume interior to the hermetic seals may under vacuum, or filled to an appropriate pressure with dry nitrogen, or one or more gases chosen for their electrical properties.

As set forth above, two fundamental approaches provide patient safety for an individual having an implanted defibrillator lead, in the presence of magnetic resonance imaging-related electromagnetic fields.

While limited examples and embodiments of the present invention have been shown and described, it will be appreciated by those skilled in the art that the spirit and scope of the present invention are not limited to the specific description and drawings herein, but extend to various modifications and changes.

What is claimed is:

1. An implanted medical device, comprising:
a cardioverter defibrillator capable of generating a pulse sufficient to defibrillate a heart of a patient; and
a lead coupled at a proximal end to the cardioverter defibrillator and having a distal end position within the heart of the patient, the distal end of the lead having a defibrillation electrode slideably coupled to a conductor and biased to be in electrical contact with the cardioverter defibrillator outside the presence of an MRI field;
wherein the defibrillation electrode slides away from the conductor in the presence of an MRI field such that induced voltages are not electrically coupled to the cardioverter defibrillator.

2. The implanted medical device of claim 1, wherein a gap is formed between the defibrillation electrode and the conductor such that the pulse arcs across the gap to defibrillate the heart while induced voltages from the MRI equipment are prevented from being electrically coupled to the cardioverter defibrillator.

3. The implanted medical device of claim 1, wherein the defibrillation electrode comprises a first member magnetically attracted to a second member in the presence of the MRI field such that a force provided by a biasing member is overcome to create a gap between the defibrillation electrode and the conductor.

4. An implanted medical device system comprising:
an implantable medical device; and
a lead coupled at a proximal end to the implantable medical device and having a distal end positioned within the heart of the patient, the distal end of the lead having an electrode slideably coupled to a conductor and biased to be in electrical contact with the implantable medical device outside the presence of a magnetic field;
wherein the electrode slides away from the conductor in the presence of a magnetic field.

5. The implanted medical device system of claim 4, wherein the electrode comprises:
a first member;
a second member that is magnetically attracted to the first member in the presence of the magnetic field; and
a biasing member that provides a force to bias the first member from the second member, wherein in the presence of the magnetic field the force provided by the biasing member is at least partially overcome to create a gap between the electrode and the conductor.

6. The implanted medical device system of claim 5, wherein the first member comprises a fixed member and the second member comprise a slideable member.

7. The implanted medical device system of claim 6, wherein the first member comprises an electrode tip.

8. The implanted medical device system of claim 5, wherein the biasing member is a spring.

9. The implanted medical device system of claim 5, wherein the magnetic attraction between the first member and the second member is dependent on a size of the magnetic field.

10. The implanted medical device system of claim 9, wherein the force provided by the biasing member is at least partially overcome to create a gap between the electrode and the conductor in the presence of a magnetic field exceeding approximately 0.05 Tesla.

11. The implanted medical device system of claim 5, wherein the first member and the second member are composed of a ferromagnetic material.

12. The implanted medical device system of claim 4, wherein the gap formed between the electrode and the conductor allows the pulse to arc across the gap to defibrillate the heart while preventing induced voltages from MRI equipment to arc across the gap.

13. The implanted medical device system of claim 4, wherein the implantable medical device comprises one of a defibrillator and a cardioverter defibrillator.

14. The implanted medical device system of claim 13, wherein the electrode comprises a defibrillation electrode.

* * * * *